United States Patent [19]

Guthauser

[11] 4,384,974

[45] May 24, 1983

[54] STABLE WATER-IN-OIL EMULSIONS

[75] Inventor: Bernadette Guthauser, North Bergen, N.J.

[73] Assignee: Revlon, Inc., New York, N.Y.

[21] Appl. No.: 61,359

[22] Filed: Jul. 27, 1979

[51] Int. Cl.$^3$ .................... B01J 13/00; A61K 47/00
[52] U.S. Cl. .................................. 252/309; 424/59; 424/170
[58] Field of Search .................. 252/309; 424/170, 59

[56] References Cited

U.S. PATENT DOCUMENTS

| | | | |
|---|---|---|---|
| 3,311,561 | 3/1967 | Anderson et al. | 252/309 X |
| 3,489,690 | 1/1970 | Lachampt et al. | 252/309 X |
| 3,565,817 | 2/1971 | Lissant | 252/310 X |
| 3,926,840 | 12/1975 | Wendler et al. | 252/309 X |
| 4,115,548 | 9/1978 | Marsh et al. | 424/170 X |

*Primary Examiner*—Richard D. Lovering

[57] ABSTRACT

Stable water-in-oil emulsions having water concentrations as high as 85% are obtained with the use of block polymer surfactants such as poloxamers and poloxamines and cosmetically acceptable surfactants having a hydrophylic-lipophilic balance of less than 10.

4 Claims, No Drawings

STABLE WATER-IN-OIL EMULSIONS

The present invention relates to emulsions. It particularly relates to stable water in oil emulsions having a high concentration of water for use in cosmetics.

Despite the undisputed benefits of water in oil (hereinafter "W/O") emulsions to the skin, a relatively small percentage of presently marketed cosmetic emulsions are of this type. This can primarily be attributed to the difficulties of maintaining the stability of W/O emulsions having a high concentration of water over a long period of time. Furthermore, such emulsions tend to have a greasy feel when being applied.

W/O emulsions have been prepared by increasing the ratio as well as the viscosity of the outer phase to improve their stability (Jr. Soc. Cosm. Chem. 28, 285 (1977)). To obtain a high concentration of water, the continuous phase; i.e., the oil phase was gelled, thereby increasing the stability. This type of formulation may be useful in preparing creams, but cannot be applied to formulate lotions because the gel, once formed, is too viscous, and the resulting emulsion although stable has poor flow qualities. Lotions are cosmetically more desirable since they are more elegant to apply, spread nicely on the skin, minimize contamination, and permit easier dispensing. (Lanzet, Cosmetic Liquid Emulsions, in The Chemistry and Manufacturing of Cosmetics, Vol. III, Pp. 379–419, Second Ed. (1975) Continental Press, Orlando, Florida.) While this publication does mention that W/O emulsions with a concentration of about 80% of water have been prepared, no information as to the procedures for formulating such emulsions is provided.

It is, accordingly, an object of the present invention to provide W/O cosmetic emulsions having a high concentration of water, which are non-greasy to the touch and are easily spread on the skin.

It is another object of the present invention to provide W/O cosmetic emulsions which remain stable during the normal shelf-life of such compositions.

It is a further object of the present invention to provide a process for the preparation of the stable W/O emulsions having a high concentration of water.

In accordance with the present invention there are provided stable W/O emulsions containing from about 45 to 85% by weight of water, which comprise water, oil, and at least two (2) surfactants, one of which must be a "block polymer", i.e., poly (oxyethylene)-poly(oxypropylene) glycol or poly(oxyethylene)-poly(oxypropylene) diamine.

The preferred block polymers are poloxamers, compounds having the formula

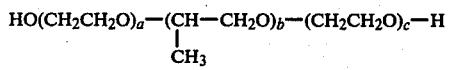

wherein a and c is each in the range of 2 to 5 and b is between about 35 to 65 (these polymers are disclosed in U.S. Pat. Nos. 2,674,619 and 2,677,700 and are sold under the trade names Pluronics L81, L101 and L121), and poloxamines, compounds having the formula

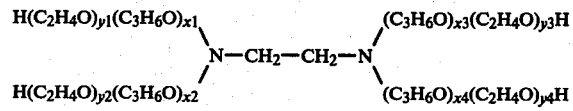

wherein y1–y4 are in the range of 3–5 and x1–x4 are in the range of 25–32 (these polymers are disclosed in U.S. Pat. No. 2,979,528 and are sold under the trade names Tetronics L1101, L1301 and L1501).

The other surfactant can be any cosmetically acceptable surfactant having a hydrophilic-lipophylic balance (as described in Jr. Soc. Cos. Chem. 1, 311 (1949) and 5. 4 (1954)) less than 10, and may be selected from any of the available anionic, cationic, amphoteric and non-ionic surfactants. These include polyvalent salts of fatty acids, sorbitol ethers, sorbitol esters, ethoxylated ether alcohols, esters of long chain fatty acids, and the like. Any commercially available surfactant can be used, provided it is cosmetically acceptable.

All oils, fats and waxes commonly used in the food, cosmetic and pharmaceutical industry can be incorporated into the emulsion systems of the present invention. These oils can be of natural or synthetic origin, consist of long chain alcohols, glyceryl esters of fatty acids or derive from fatty esters of monohydric alcohols. These esters and alcohols can be straight or branch chained, saturated or unsaturated and the number of carbon atoms may range from $C_{12}$ to $C_{36}$. The selection of the oil vehicle depends entirely upon the purpose of the emulsion. For example, (1) For a light lotion or cream, a so-called "moisturizing emulsion", the oil vehicle preferably consists of hydrophilic oils branch chained saturated or unsaturated esters or alcohols derived from low to medium molecular weight fatty acids such as isopropyl myristate, 2-octyl dodecanol.

(2) For a slightly heavier lotion with emphases on moisturizing and emollient properties, the oil vehicle may consist of hydrocarbons, oils and fats of vegetable or animal origin, or a mixture thereof, such as mineral oil, sunflower oil, lanolin derivatives.

(3) For highly emollient emulsions, where more occlusive properties are desired, the oil vehicle preferably contains some mineral oil or petrolatum or esters of higher fatty acids such as oleyl oleates ($C_{36}H_{68}O_2$).

(4) If the lotion has a purpose other in to impart moisture and emolliency to the skin, the corresponding active ingredient can be incorporated into the oil phase; such a case would be a sun protection emulsion where one or more commercially available sunscreen agents can be added to the oil phase.

The compositions of the present invention are in weight percent as follows:
Water: 45–85
Oil: 1–50
Block polymer surfactant: 1–30
Other surfactant: 0.1–22

The preferred compositions contain in weight percent:
Water: 70–80
Oil: 10–20
Block polymer surfactant: 2–15
Other surfactant: 0.5–15

In addition to the four (4) essential ingredients the cosmetic composition may contain thickeners such as, for example, lanolin, beeswax, synthetic gelling agents such as stearalkonium hectorites, poly-ethylenes, and colloidal silicas, colorants, fragrances and preservatives.

The inherent stability of the emulsions of this invention eliminates undesirable additional steps normally required in the manufacture of W/O emulsions. There is no special need for homogenization of the emulsion either during emulsification or after formation of the product.

In preparing the compositions of the present invention the two (2) types of surfactants and any other oil-soluble materials are introduced into the oil phase and stirred (with warming if necessary) to bring the materials into solution. Any water-soluble materials such as, for example, humectants and preservatives are dissolved in the water phase. The two (2) phases are then mixed and stirred vigorously for at least 15 minutes. If heat has been used to effect solution of materials in either the oil or water phases, the temperature of the heated phase is reduced to about 70° to 80° C. before mixing.

By following the above procedure stable emulsions as described in the following examples were obtained. These examples are given by way of illustration and are not to be considered as limiting.

Examples 1 to 3 illustrate the general compositions of the lotions, and Examples 4 to 9 emulsions for specific uses.

EXAMPLE I

Pluronic L121: 4.0%
Magnesium Stearate: 0.1
Polyethylene 617A: 1.0
Isopropyl Myristate: 9.4
Preservatives: 0.5
Water: 85.0

EXAMPLE II

Pluronic L121: 21.4%
Magnesium Stearate: 0.1
Preservatives: 0.5
Propylene Glycol: 3.0
Water: 74.0
Isopropyl Stearate: 1.0

EXAMPLE III

Pluronic L121: 1.0%
Span 65: 2.0
Bentone 27 Gel In IPM: 5.0
Preservatives: 0.5
Propylene Glycol: 3.0
Water: 75.0
Isopropyl Myristate: 13.5

EXAMPLE IV

MASSAGE CREAM FOR FACE AND BODY

Tetronic 1501: 10.0%
Arlacel 60: 1.0
Zinc Stearate: 2.0
Polyethylene 617A: 2.0
Propylene Glycol Monoisostearate: 6.0
Mineral Oil 65/75: 25.0
White Petrolatum: 4.0
Preservatives: 0.5
Propylene Glycol: 3.0
Water: 46.5

EXAMPLE V

MAKE-UP REMOVER

Pluronic L121: 5.0%
Arlacel 65: 2.0
2-Octyl Dodecanol: 4.0
Propylene Glycol Monoisostearate: 4.0
Mineral Oil-Bentone Gel: 15.0
Isopropyl Myristate: 8.0
Preservatives: 0.5
Propylene Glycol: 3.0
Water: 58.5

EXAMPLE VI

UNDER MAKE-UP LOTION

Pluronic L121: 4.0%
Zinc Stearate: 1.0
Talc: 1.0
Isostearyl Neopentonate: 5.0
Isopropyl Myristate: 5.5
Propylene Glycol Diesters of C8–10: 5.0
Fatty Acids:
Preservatives: 0.5
Propylene Glycol: 3.0
Water: 75.0

EXAMPLE VII

DAYTIME MOISTURIZING LOTION

Pluronic L121: 6.0%
Propylene Glycol Hydroxystearate: 1.0
Isopropyl Myristate: 14.5
Preservatives: 0.5
Propylene Glycol: 3.0
Water: 75.0

EXAMPLE VIII

PROTECTIVE SPORTS LOTION WITH SUNSCREEN AGENTS

Pluronic L121: 4.0%
Triglyceryl diisostearate: 0.8
Isopropyl Isostearate: 2.0
Polyethylene 617A: 1.0
Oleyl Alcohol: 5.0
Mineral Oil: 3.2
Octyl Dimethyl PABA: 3.0
2-Hydroxy-4-Methoxy Benzophenone: 2.5
Preservatives: 0.5
Propylene Glycol: 3.0
Water: 75.0

EXAMPLE IX

ALL PURPOSE SKIN CLEANSING LOTION

Pluronic L121: 4.0%
Magnesium Stearate: 1.0
Oleyl Alcohol: 5.0
Mineral Oil: 11.5
Preservatives: 0.5
Propylene Glycol: 3.0
Water: 75.0

EXAMPLE X

HAND AND BODY LOTION

Pluronic L121: 6.0%
Propylene Glycol Hydroxystearate: 1.0
Lanolin Acid: 2.0

Stearyl Alcohol: 1.0

Propylene Glycol Dicaprylate/Dicaprate: 11.1

Preservatives: 0.5

Magnesium Sulfate: 0.4

Propylene Glycol: 3.0

Water: 75.0

I claim:

1. A stable water-in-oil emulsion comprising in weight percent water: about 70–80 oil: about 10–20 a block polymer surfactant: about 2–15, and a cosmetically acceptable surfactant: about 0.5–15 wherein the block polymer surfactant is selected from the group consisting of polymers of the formula

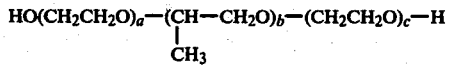

wherein a and c are in the range of 2 to 5 and b is between 35–65, and

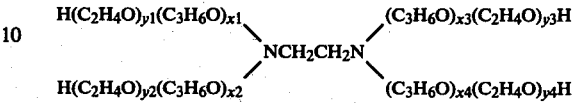

wherein y1 to y4 are in the range of 3 to 5 and x1 to x4 are in the range of 25 to 32, and the cosmetically acceptable surfactant has a hydrophilic-lipophilic balance of less than 10.

2. A stable water-in-oil emulsion according to claim 1 wherein the block polymer surfactant is a poloxamer.

3. A stable water-in-oil emulsion according to claim 2 wherein the oil is isopropyl myristate.

4. A stable water-in-oil emulsion according to claim 1 wherein the block polymer surfactant is a poloxamine.